US00PP20948P2

(12) United States Plant Patent
Boehm

(10) Patent No.: US PP20,948 P2
(45) Date of Patent: Apr. 27, 2010

(54) ***SCHIZACHYRIUM* PLANT NAMED 'CAROUSEL'**

(50) Latin Name: *Schizachyrium scoparium*
Varietal Denomination: Carousel

(76) Inventor: Donovan L. Boehm, Boehm's Garden Center, 708 Macomb Rd., Rushville, IL (US) 62681

( * ) Notice: Subject to any disclaimer, the term of this patent is extended or adjusted under 35 U.S.C. 154(b) by 0 days.

(21) Appl. No.: 12/319,824

(22) Filed: Jan. 13, 2009

(51) Int. Cl.
*A01H 5/00* (2006.01)

(52) U.S. Cl. ..... Plt./384
(58) Field of Classification Search ..... Plt./384
See application file for complete search history.

*Primary Examiner*—Kent L Bell
(74) *Attorney, Agent, or Firm*—Penny J Aguirre

(57) ABSTRACT

A new cultivar of *Schizachyrium scoparium,* 'Carousel', that is characterized by its compact and rounded form with upright culms that does not lodge in fall and winter or with exposure to rain or snow, its short stature with a height of about 30 cm, its foliage that emerges nearly horizontal and becomes upright, its coloration that is green to blue-green with streaks of pink in summer, a blend of copper, beige, orange-red, and mahogany in fall, and beige in winter.

2 Drawing Sheets

Botanical classification: *Schizachyrium scoparium.*
Varietal denomination: 'Carousel'.

BACKGROUND OF THE INVENTION

The present invention relates to a new and distinct cultivar of *Schizachyrium scoparium* and will be referred to hereafter by its cultivar name, 'Carousel'. 'Carousel' represents a new cultivar of little bluestem, an ornamental grass grown for landscape use.

The Inventor discovered and selected the new cultivar, 'Carousel', in a garden plot that had been planted with 200 seedlings derived from open-pollination of unnamed plants of *Schizachyrium scoparium* in the summer of 1998 in Rushville, Ill. 'Carousel' was selected as a single plant amongst the seedlings for its unique characteristics and suitability as a landscape plant.

Asexual reproduction of the new cultivar was first accomplished by culm division in Rushville, Ill. in 2002 by the Inventor. The vegetative propagules of this cultivar have been determined to be stable and are reproduced true to type in successive generations.

SUMMARY OF THE INVENTION

The following traits have been repeatedly observed and represent the characteristics of the new cultivar. These attributes in combination distinguish 'Carousel' from any known selections of *Schizachyrium scoparium* known to the Inventor.

1. The plant growth habit of 'Carousel' is compact and rounded with upright culms that do not lodge in fall and winter or with exposure to rain or snow. The habit of the species is much looser and open, with arching and lodging typical.
2. The mature plant height of 'Carousel' is about 30 inches (76 cm), which is shorter than most little bluestem as the species typically reaches 3 to 4 feet (90 to 120 cm) in height.

3. The new foliage emerges nearly horizontal; the new foliage of the species emerges upright.
4. 'Carousel' exhibits coloration that is green to blue-green with streaks of pink in summer, a blend of copper, beige, orange-red, and mahogany in fall, and turns to beige in winter.
5. The winter foliage and flowering stems are retained throughout the winter months.

The species, *Schizachyrium scoparium*, differs from 'Carousel' in being taller in height and having a more upright, arching habit that typically lodges in late fall and winter. 'Carousel' can be compared to cultivars, 'The Blues' (not patented), 'Blaze' (not patented), and 'MinnblueA' (U.S. Plant Pat. No. 17,310). Both 'The Blues' and 'Blaze' differ from 'Carousel' in having a more upright and taller plant habit and having foliage that will lodge in winter. 'MinnblueA' is similar to 'Carousel' in having foliage that remains upright without lodging in winter, however 'MinnblueA' differs from 'Carousel' in being much taller in height and in exhibiting a narrow and upright plant habit.

BRIEF DESCRIPTION OF THE DRAWINGS

The accompanying photographs were taken in central Illinois and illustrate the characteristics of 2 year-old plants the new cultivar, 'Carousel', as grown outdoors in trial gardens.

The photograph in FIG. 1 depicts the plant habit and foliage coloration of 'Carousel' as observed in July.

Figure 1:
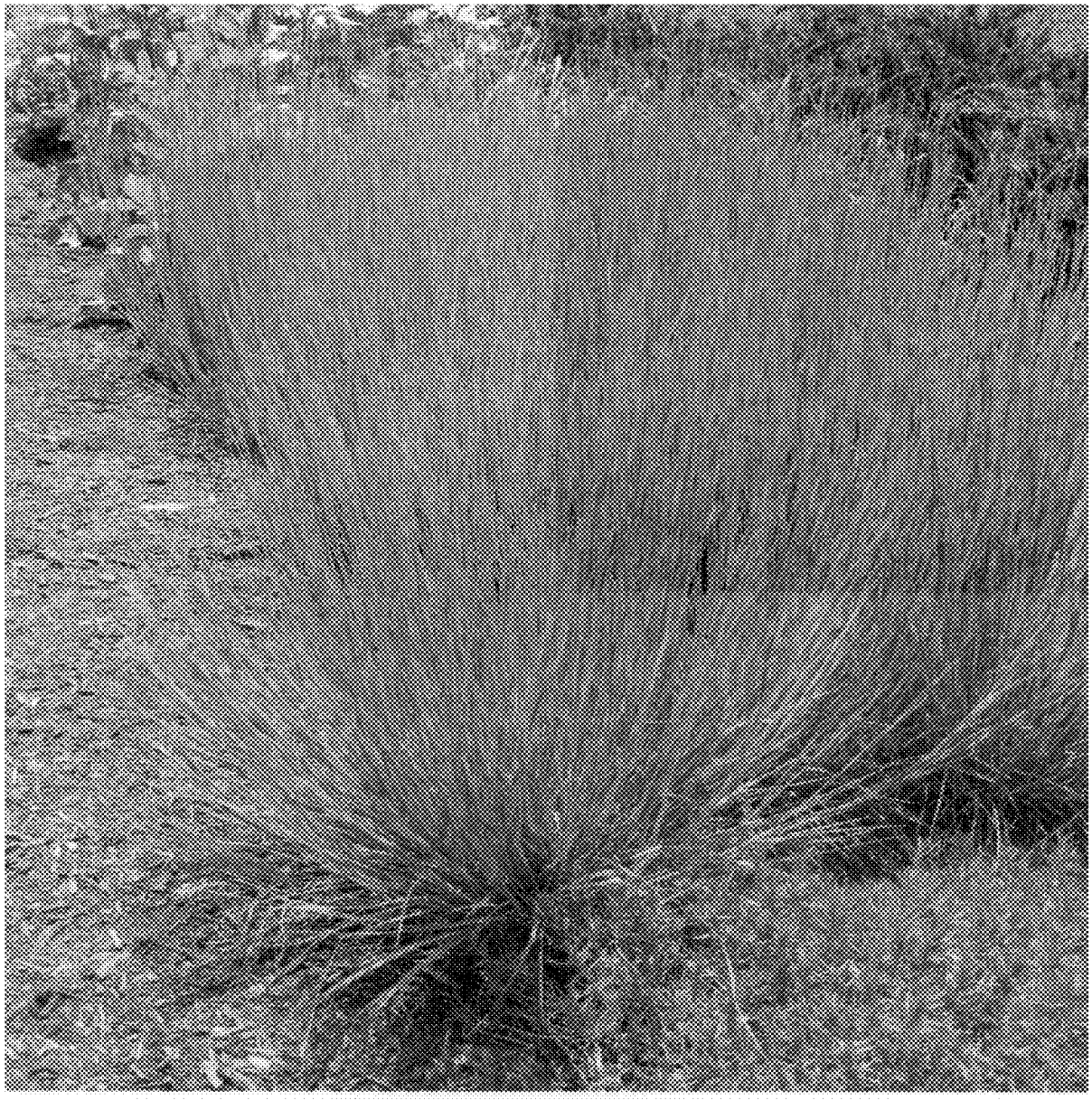
Figure 2:
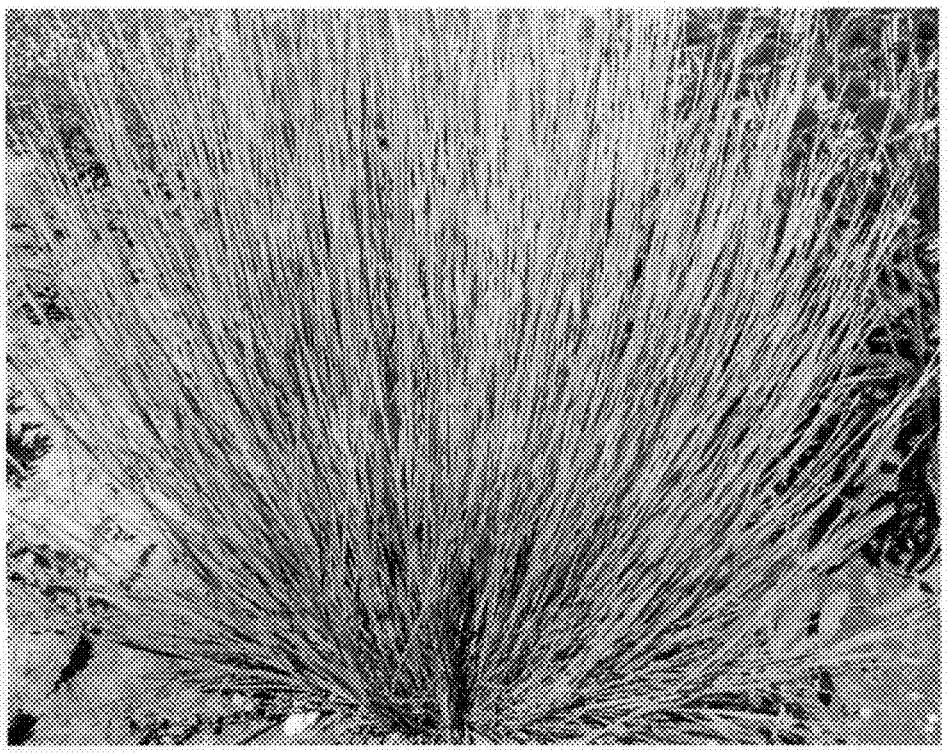

The photograph in FIG. 2 depicts the plant habit and foliage coloration of 'Carousel' as observed in September.

Figure 3:
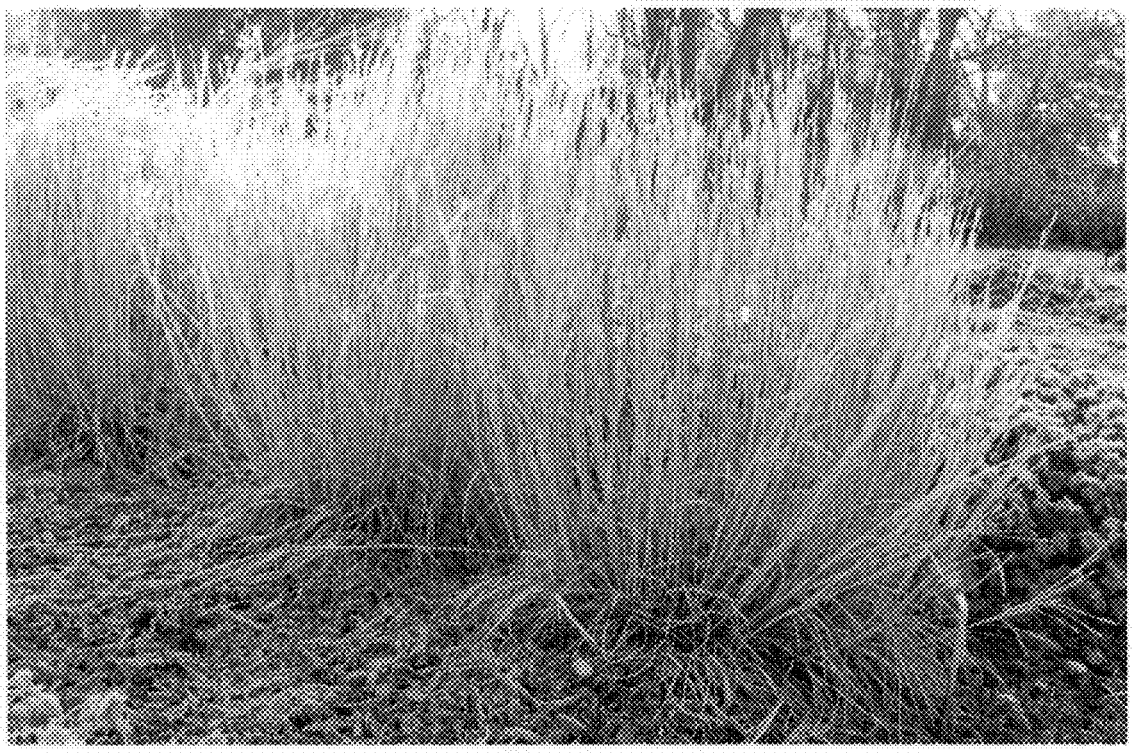

The photograph in FIG. 3 depicts the plant habit and foliage coloration of 'Carousel' as observed in winter.

The colors in the photograph may differ slightly from the color values cited in the detailed botanical description, which accurately describe the colors of the new *Schizachyrium.*

DETAILED BOTANICAL DESCRIPTION

The following is a detailed description of the new cultivar as observed for ten years in Rushville and Glencoe, Ill. with the detailed data collected on plants two years in age as grown in a garden in New Hope, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—August and September in Illinois with seed head persistent.

*Plant habit.*—Herbaceous perennial grass, compact and rounded with upright culms that do not lodge in fall and winter or with exposure to rain or snow.

*Height and width or spread.*—Reached about 30 inches (76 cm) in height and spread.

*Hardiness zone.*—U.S.D.A. Zones 3–9.

*Diseases and pests.*—*Schizachyrium scoparium* is relatively free of disease. No susceptibility of resistance to disease or pests has been observed.

*Root description.*—Fibrous, wiry, deep rooted.

Growth and propagation:

*Propagation.*—Root division, probably basal stem cuttings and tissue culture.

*Growth rate.*—Moderate.

Culm (stem) description:

*General.*—Cylindrical, solid, thin but strong, emerge horizontal in spring and becoming nearly erect for the remainder of the year.

*Culm color.*—182B to 182D in summer, N97B to 175C in fall, 161D to 158A in winter, ranges from 2 to 3.5 cm of exposed area between leaf nodes.

*Culm size.*—Average of 2 mm in diameter, averaging 30 cm in height from the base to the tip of the flower panicle.

*Culm surface.*—Glabrous with sheathes villous.

*Internode length.*—6 to 9 cm.

Foliage description:

*Leaf shape.*—Linear, sparsely pilose at their junction, flat.

*Leaf division.*—Simple, margins entire.

*Leaf base.*—Sheathed to base of the node.

*Leaf venation.*—Parallel, not distinguishable in color from leaf.

*Leaf width.*—Average of 4 mm.

*Leaf length.*—Basal leaves average of 23 cm, near the apex of the culm average of 7.5 cm.

*Leaves per culm.*—Average of 4.

*Leaf surface.*—Glabrous.

*Ligule.*—1 mm in width, membranous, 161D in color.

*Leaf color.*—Summer; 138A to 138B, Fall; ranging from 166B to 166D to N177B, winter; 161D to 158A.

Flower description:

*Inflorescence type.*—Multiple, typically 3–5, racemes present per node, typically on upper 3 nodes. Rachis is about 11 cm in length and 0.3 mm in width with racemes of spikelets arranged alternately on upper 4 cm in length. Spikelets are appressed to the rachis and appear sessile, rachis is 165C in color and the overall mature color of the raceme is 161D becoming 161D to 158A in winter.

*Spikelet description.*—Average of 9 per raceme, equal glumes 7 mm in length and 1 mm in width and 144B in color, lemma extending into very fine flexuous awn, 5 mm in length 144B in color with fine awn about 8 mm in length, palea small and hyaline.

*Spikelet size.*—About 1.8 cm in length with awn and 1 mm in width.

*Spikelet hairs.*—Emerging from the base as a tuft surrounding the base, average of 2 mm in length, very fine, 155B in color.

Reproductive organs:

*Androecium.*—Anthers; 3, 3 mm in length and 0.7 mm in width, 145C in color, basifixed on very fine filament extending about 1.5 mm from spikelet, Pollen; abundant, N186B in color.

*Gynoecium.*—Pistil; 1, 2 plumose stigmas on short, file styles, stigma color is 76A, 2 mm in length and 1 mm in width, ovary; 1-locular, superior, minute, not easily quantifiable in size and color.

*Caryopsis.*—Lemma and palea adhering to the caryopsis, actual caryopsis very small and fine, less than 1mm.

It is claimed:

1. A new and distinct cultivar of *Schizachyrium* plant named 'Carousel' as herein illustrated and described.

* * * * *